United States Patent
Martin et al.

(10) Patent No.: US 7,022,693 B2
(45) Date of Patent: Apr. 4, 2006

(54) TREATMENT OF LIPODYSTROPHY

(75) Inventors: John Francis Martin, London (GB); Jorge D. Erusalimsky, London (GB); Hugh Edward Montgomery, London (GB)

(73) Assignee: Ark Therapeutics Ltd., (GB)

( * ) Notice: Subject to any disclaimer, the term of this patent is extended or adjusted under 35 U.S.C. 154(b) by 0 days.

(21) Appl. No.: 10/485,018

(22) PCT Filed: Aug. 7, 2002

(86) PCT No.: PCT/GB02/03639

§ 371 (c)(1),
(2), (4) Date: May 20, 2004

(87) PCT Pub. No.: WO03/013486

PCT Pub. Date: Feb. 20, 2003

(65) Prior Publication Data

US 2004/0209941 A1  Oct. 21, 2004

(30) Foreign Application Priority Data

Aug. 9, 2001 (GB) ................................... 0119460

(51) Int. Cl.
*A61K 31/55* (2006.01)
*A61K 31/47* (2006.01)
*A61K 31/40* (2006.01)
*A61K 31/195* (2006.01)

(52) U.S. Cl. ................. 514/212.07; 514/212; 514/307; 514/409; 514/412; 514/423; 514/563

(58) Field of Classification Search ........... 514/212.07, 514/221, 307, 409, 412, 423, 563
See application file for complete search history.

(56) References Cited

U.S. PATENT DOCUMENTS

2004/0082496 A1 * 4/2004 Acton et al. .................... 514/1
2004/0087645 A1 * 5/2004 Scholkens et al. .......... 514/423

FOREIGN PATENT DOCUMENTS

EP 0635263 A2 5/1994
WO WO 99/20260 A 4/1999
WO WO 01/96347 A1 12/2001

OTHER PUBLICATIONS

Bonora, E. et al. "Effect of chronic treatment with lacidipine or lisinopril on intracellular partitioning of glucose metabolism in type 2 diabetes mellitus," *J. Clin. Endocrinolo. Metab.* (1999), vol. 84, No. 5, pp. 1544-1550. Abstract from Database DrugU 'Online!.

Burns, G.C., et al. "Effect of Angiotensin-Converting Enzyme Inhibition in HIV-Associated Nephropathology," *Journal of the American Society of Nephrology* (1997), vol. 8, No. 7, pp. 1140-1146.

Caldiz, C. et al. "Insulin Resistance in Adipocytes From Spontaneously Hypertensive Rats: Effect on Long-Term Treament with Enalapril and Losartan," *Metabolism* (1999), vol. 48, No. 8, pp. 1041-1046.

Chisholm, D. et al. "Pathogenisis of the Insulin Resistance Syndrome (Syndrome X)," *Clinical and Exp. Pharm. And Physiol.* (1997), vol. 24, Nos. 782-784.

Chow, L. et al. "Blockade of angiotensin converting enzyme but not of angiotensin $AT_1$ receptors improves glucose tolerance," *European Journal of Pharmacology* (1997), vol. 319, pp. 77-83.

Duong, M. et al. "Coronary Heart Disease associated with the use of human immunodeficiency virus (HIV)-1 protease inhibitors: Report of Four Cases and Review," *Clinical Cardiology* (2000), vol. 24, pp. 690-694.

Egan, B. et al. "Effects of NaCl Restriction and Converting Enzyme Inhibition on Insulin and Blood Pressure in Hypersensitive Men with Upper Body Obesity," *Clin. Res.* (1991), vol. 39, No. 2, pp. 432A.

Hardy, H. et al. "Glucose Disorders Associated with HIV and Its Drug Therapy," *Infectious Diseases* (2001), vol. 35, pp. 343-351.

Hasslacher, C. "ACE-Hemmer bei metabolischem Syndrom," *Zeitschrift for Kardiologie* (1994), vol. 83, Supplement 4, pp. 21-29.

(Continued)

*Primary Examiner*—Raymond J. Henley, III
(74) *Attorney, Agent, or Firm*—Saliwanchik, Lloyd & Saliwanchik

(57) ABSTRACT

An inhibitor of the renin-angiotensin system is useful for the treatment or prevention of the lipodystrophy syndrome, e.g. in AIDS patients also receiving anti-retroviral therapy.

6 Claims, No Drawings

OTHER PUBLICATIONS

Memon, A. et al. "Long term renal survival in HIV-associated nehropathy (HIVAN) with highly active antiretroviral therapy and angiotensin-converting enzyme inhibitors (ACEI)," *Journal of the American Society of Nephrology* (2000), vol. 11, Program and Abstract Issue, p. 91A.

Narciso, P. et al. "Metabolic and Morphologic Disorders in Patients Treated with Highly Active Antiviral Therapy since Primary HIV Infection," *Annals of the New York Academy of Sciences* (Nov., 2001), vol. 946, pp. 214-222.

Nawano, M. et al. "Imidapril, an angiotensin-converting enzyme inhibitor, improves insulin sensitivityby enhancing signal transduction via insulin receptor substrate proteins and improving vascular resistance in the Zucker Fatty Rat," *Metabolism* (1999), vol. 48, No. 10, pp. 1248-1255.

Radin, M. et al. "Treatement of Obese female an male SHHF/Mcc-facp rats with Antihypertensive Drugs, Nifedipine and Enalapril: Effects on Body Weight, Fat Distribution, Insulin Resistance and Systolic Pressure," *Obesity Research* (1993), vol. 1, No. 6, pp. 433-442.

Suter, P. et al. "Metabolic Effects of Antihypertensive Drugs, " *Journal of Hypertension* (1995), vol. 13, Supplement 4, pp. S11-S17.

Verges, B. and Petit, J.M. "Anomalies lipidiques au cours des traitements par antiproteases," *Presse Med* (2001), vol. 30, pp. 911-914.

* cited by examiner

TREATMENT OF LIPODYSTROPHY

This application is a National Stage Application of International Application Number PCT/GB02/03639, published Aug. 7, 2002, pursuant to PCT Article 21(2); which claims priority to Great Britain Application GB 0119460.4, filed Aug. 9, 2001.

FIELD OF THE INVENTION

This invention relates to the treatment of lipodystrophy, especially in HIV-infected patients and in AIDS patients undergoing anti-retroviral therapy.

BACKGROUND OF THE INVENTION

With the introduction of highly active anti-retroviral therapy (HAART) in 1996, the typical cachexia associated with AIDS has fallen sharply, and the development of a new metabolic condition called "the lipodystrophy syndrome" has occurred. This new metabolic syndrome which affects HIV-infected patients receiving triple HAART was first described only recently, and is thought to be either an extension of the cachexia state or an adverse effect of the HAART treatment.

The main clinical features of the lipodystrophy syndrome are peripheral fat loss, central fat accumulation and metabolic abnormalities which lead to lactoacidosis. The overall incidence of these physical abnormalities in recent reports and in abstracts presented at 1999 AIDS meetings is about 50% after 12–18 months of therapy. The differences between these prevalence rates range from 18% to 83% due to confounding factors such as type and duration of anti-retroviral therapy and the lack of an objective and validated case definition.

The metabolic features associated with lipodystrophy and protease-inhibitor therapy include hypertriglyceridaemia, hypercholesterolaemia, insulin-resistance, type II diabetes mellitus and lactoacidosis. Dyslipidaemia at concentrations associated with increased cardiovascular disease occurs has been reported in about 70% of HIV patients receiving HAART. These metabolic abnormalities are more profound in those patients whose HAART regimen includes a protease inhibitor. More recently, peripheral fat loss has also been associated with low-grade lactic acidaemia liver dysfunction, but in the absence of lipid or glycaemic changes.

The metabolic changes of lipodystrophy may have serious clinical consequences. Several reports have described premature coronary-artery disease in patients with few or no risk factors that were receiving protease inhibitors. The increase in risk has been estimated from available metabolic data to be 1.4 cardiac events per 1000 patient-years.

It has been suggested that the lipodystrophy syndrome associated with protease inhibitors may be due to partial analogy between lipid and adipocyte regulatory proteins and the catalytic site of HIV-1 protease to which these protease inhibitors bind (Carr et al, Lancet 1998; 351:1881–83). In vitro studies have shown that protease inhibitors can inhibit lipogenesis (Zhang et al, J. Clin. Endocrinol. Metab. 1999; 84:4274–77, and Lenhard et al, Biochem Pharmacol 2000; 59:1063–68).

More recently, some features of this syndrome have been suggested to represent mitochondrial toxicity of nucleotide analogue reverse transcriptase inhibitors (NRTIs). Peripheral lipoatrophy with fat redistribution in association with hyperlactaemia has been reported in patients who received only NRTIs. These changes also occur in HIV-uninfected patients with mitochondrial defects.

The results from a study investigating the underlying effect of HIV-1 on metabolic and body composition parameters concluded that the metabolic abnormalities of the HAART-associated lipodystrophy syndrome may be related to the HIV-1 infectious process or to factors associated with immunological dysfunction (Shikuma et al, AIDS 1999; 13:1359–65). Another study of HIV-positive subjects receiving HAART revealed that lipodystrophy may result from the accumulation of T cells with impaired apoptosis, which are primed for TNF alpha synthesis (Ledru et al, Blood 2000; 95(10):3191–8). Protease inhibitors themselves have also been shown to impair T cell apoptosis (Sloand et al, Blood 1999; 94(3):1021–7).

The renin-angiotensin system (RAS) and its components are known and may be described as follows. Briefly, cells of the renal juxta-glomerular apparatus produce the aspartyl protease renin which acts on the alpha-2 globulin angiotensinogen (synthesised in the liver) to generate angiotensin I (AI). This non-pressor decapeptide is converted to angiotensin II (ATII) by contact with the peptidyldipeptidase angiotensin-converting enzyme (ACE). ATII stimulates the release of aldosterone, and is also a potent vasoconstrictor. The renin-angiotensin system is therefore important in the maintenance and control of blood pressure as well as the regulation of salt and water metabolism. Renin, angiotensinogen and ACE have also been identified in cardiovascular tissues including the heart and blood vessels, as has mRNA for components of this system such as angiotensinogen. Receptors for angiotensin II have been found on vascular smooth muscle cells. Within tissues, the RAS may therefore have a local paracrine function, and the expression of the different components can be altered by pathophysiological stimuli such as sodium restriction. Kinetic studies suggest that much of the circulating angiotensin I and II is derived from the both renal and non-renal tissues.

There are many marketed or investigation-stage agents which inhibit RAS activity, and many of them fall into two broad classes: inhibitors of angiotensin-converting enzyme, whose approved names generally end in "pril" or in the case of active metabolites "prilat", and antagonists at angiotensin receptors (more specifically, currently, the $AT_1$ receptor), whose approved names generally end in "sartan". Also potentially of increasing importance may be a class of drugs known as neutral endopeptidase inhibitors, some of which will also have an ACE-inhibitory effect or the potential to reduce RAS activity.

WO 99/20268 discloses that ACE inhibitors can enhance the performance of those undergoing exercise, and suggests various therapeutic uses for such compounds, including the treatment of cachexia.

SUMMARY OF THE INVENTION

The present invention is based on an understanding of how conventional anti-retroviral therapy may be associated with the lipodystrophy syndrome. In particular, it has been found that the administration of a protease inhibitor (bestatin) is associated with increased ACE activity in T-cells. While not wishing to be bound by theory, this finding may help explain the mechanism by which anti-retroviral therapy results in lipodystrophy. If anti-retroviral therapy results in over-expression of ACE, the increased levels of ACE may be a causative factor in lipodystrophy, due to its known effects on metabolism, as discussed above. The mechanism by which inhibitors of the renin-angiotensin system operate, can be utilised to counteract certain deleterious effects of anti-retroviral therapy.

Therefore, the present invention is based on the realisation that inhibitors of the renin-angiotensin system may be used the therapy of lipodystrophy in AIDS patients undergoing anti-retroviral therapy.

According to a first aspect of the invention, an inhibitor of the renin-angiotensin system is used in the manufacture of a medicament for the treatment or prevention of the lipodystrophy syndrome.

According to a second aspect of the invention, an inhibitor of the renin-angiotensin system is used in the manufacture of a medicament for the co-administration to a patient being administered a protease inhibitor and/or a reverse transcriptase inhibitor, for the treatment or prevention of a condition associated with a decrease in metabolic function.

The invention can provide an effective treatment for the lipodystrophy syndrome, and therefore offers an improvement in conventional AIDS therapy, with obvious benefit to the patient being treated.

DESCRIPTION OF THE PREFERRED EMBODIMENTS

Having described the various components of the RAS above, it will be apparent that the system can be inhibited at various points. In principle, it is expected that any sufficiently non-toxic compound which is bioavailable and active to inhibit the RAS system at any suitable point can be used in the invention. This invention contemplates the administration of all such agents (either singly or in combination with each other and/or with other classes of pharmacological agents), and also of pro-drugs which are converted in vivo to an active agent which inhibits RAS activity. Note that RAS inhibition need not be total inhibition; rather, sufficient inhibition to be beneficial in the invention is all that is required. In practice, it is preferred at the present state of knowledge to use in the practice of the invention any of the known RAS inhibitors which are either on the market or under investigation for their antihypertensive effects.

Many inhibitors of the renin-angiotensin system are licensed or under investigation for use in humans in the United Kingdom and are compounds whose use is preferred in the practice of the invention. They include the ACE-inhibitors Quinapril, Captopril, Lisinopril, Perindopril, Trandolapril, Enalapril, Moexipril, Fosinopril, Ramipril, Cilazapril, Imidapril, Spirapril, Temocapril, Benazepril, Alacepril, Ceronapril, Cilazapril, Delapril, Enalaprilat and Moveltipril. Suitable angiotensin II-inhibitors include Losartan, Valsartan, Irbesartan, Candesartan, Eprosartan, Tasosartan and Telmisartan.

The specific compounds listed may be useful in accordance with the invention in their free form, for example as the free acid or base as the case may be, and they may be useful as acid addition salts, esters, N-oxides or other derivatives as appropriate. The use of suitable pro-drugs (whether themselves active or inactive) and the use of active metabolites of RAS inhibitors are also within the scope of the invention. For example, alacepril is a pro-drug for captopril, and enalaprilat is an active metabolite of enalapril.

Although ACE inhibitors and angiotensin II-receptor antagonists are presently the most widely developed classes of drugs suitable for use in the present invention, the invention is by no means limited to their use.

ACE inhibitors may work through both a reduction in ATII formation and through a reduction in kinin metabolism. Other agents may also inhibit kinin degradation, and as such have similarly beneficial effects. These classes of drugs include inhibitors of neutral endopeptidases, some of which also of ACE-inhibitory properties. The invention thus contemplates the use of all kininase-inhibitors and kinin receptor antagonists (such as bradykinin).

The compounds for use in the invention are preferably lipophilic. However, the invention contemplates the use of compounds which are essentially non-lipophilic, or only moderately lipophilic, but which have been rendered more lipophilic either chemically, such as by appropriate derivatisation, or physically, such as by formulation with lipophilic carriers or delivery systems.

Administration of the active agent may be by any suitable route. As is conventional for ACE inhibitors at least, oral administration may be preferred, especially for the purposes of achieving a prophylactic or preventative effect. In certain circumstances, especially when a more immediate effect is required, intravenous administration may be preferred. Suitable formulations for intravenous administration will be evident to those skilled in the art.

The optimum frequency of dosage and duration of treatment may also be established experimentally and/or clinically. Again by way of example, oral imidapril may be given once daily for an appropriate period of time. Frequencies of dosage for other compounds useful in the invention will vary, and will depend on, among other things, the pharmacokinetics of the compound in question.

In a preferred embodiment, the inhibitor is administered more than once a day in order to avoid peak inhibition of plasma ACE activity whilst maximising tissue concentration. Alternatively, an oral, subcutaneous or intramuscular slow release formulation may be provided to achieve the same effect.

The preferred therapy is for patients being co-administered anti-retroviral therapy. The patients are most likely therefore to be HIV-infected (without AIDS symptoms) or suffering from AIDS. The anti-retroviral therapy may be protease inhibitors and/or nucleoside analogue reverse transcriptase inhibitors. The anti-retroviral compounds do not need to be administered at the same time as the inhibitors of the renin-angiotensin system. It is sufficient that the patient has been administered the anti-retrovirals. It is also not necessary that the patient is actually suffering from cachexia modified by lipodystrophy or the lipodystrophy syndrome, as the intended therapy may have a prophylactic effect.

The following study is intended to illustrate the utility of the invention.

In order to evaluate the invention, a multi-centre, double-blind, placebo-controlled, randomised, parallel group, study is conducted. Patients are evaluated at a screening visit for signs of lipodystrophy as assessed by a patient and investigator questionnaire. Subjects considered eligible have a fasting blood sample taken for the measurement of serum triglyceride and ACE genotyping. In addition, blood samples are drawn for glucose, NEFA and insulin measurements at 0 (after at least an 8 hour fast), 15, 30, 60 and 120 mins after an oral glucose load.

Patients are randomised into two groups: 25 patients receive three times daily treatment with placebo, and 25 patients receive three times daily treatment with imidapril hydrochloride (6.66 mg dose).

Each patient is tested on seven more occasions during the study, at 1, 2, 3, 4, 8 and 12 weeks after the start of treatment, and again for a safety evaluation between 7 and 14 days of the last visit.

At all post-baseline visits, a fasting blood sample is drawn for clinical chemistry and haematology. At week 12, glucose, NEFA and insulin levels are again measured at 0 (after an 8 hour fast), 15, 30, 60 and 120 mins after an oral glucose load.

At all visits except weeks 1 and 3, weight, lean body mass, percentage body fat, waist, hip, thigh and arm circumferences, and skinfold thickness are measured using bioimpedence and anthropomorphic methods. Vital signs (blood pressure and heart rate) and compliance with the study medication are measured at each visit. At weeks 8 and 12, the patient and physician are required to complete another questionnaire. At week 12, another full body DEXA scan is taken (no later than five days after the end of treatment).

Patients who withdraw from the study prior to the week 12 visit complete all assessments in the week 12 visit. The withdrawal assessment takes place as soon as possible after stopping treatment but no more than 7 days after withdrawal. All subjects have a safety evaluation conducted 1–2 weeks after discontinuation of study drug.

Since imidapril is an antihypertensive agent, dose-dependent decreases in blood pressure may be observed. All patients receive 6.66 mg of imidapril hydrochloride or matched placebo three times daily. If the 6.66 mg dose level of imidapril hydrochloride or matched placebo is not tolerated, the dose may be decreased to 3.33 mg three times daily for the duration of the study. If the 3.33 mg dose level of imidapril hydrochloride or matched placebo is not tolerated, the patient is withdrawn.

The invention claimed is:

1. A method for the treatment of lipodystrophy syndrome wherein said method comprises administering, to a patient in need of such treatment, an effective amount of an inhibitor of the renin-angiotensin system, wherein the inhibitor of the renin-angiotensin system is selected from the group consisting of quinapril, captopril, lisinopril, perindopril, trandolapril, enalapril, moexipril, fosinopril, ramipril, cilazapril, imidapril, spirapril, temocapril, benazepril, alacepril, ceronapril, cilazapril, delapril, enalaprilat, moveltipril, losartan, valsartan, irbesartan, candesartan, eprosartan, tasosartan, and telmisartan; and wherein the lipodystrophy syndrome is in a patient undergoing anti-retroviral therapy.

2. The method according to claim 1, wherein the anti-retroviral therapy is the administration of a protease inhibitor and/or a reverse transcriptase inhibitor.

3. The method according to claim 1, wherein the inhibitor of the renin-angioten system is lipophilic.

4. The method according to claim 1, wherein the inhibitor of the renin-angioten system is imidapril.

5. The method according to claim 1, wherein the inhibitor of the renin-angiotensin system is an angiotensin receptor antagonist.

6. The method according to claim 5, wherein the angiotensin receptor antagonist is an angiotensin II receptor antagonist.

* * * * *

UNITED STATES PATENT AND TRADEMARK OFFICE
CERTIFICATE OF CORRECTION

PATENT NO. : 7,022,693 B2
APPLICATION NO. : 10/485018
DATED : April 4, 2006
INVENTOR(S) : John Francis Martin, Jorge Daniel Erusalimsky and Hugh Edward Montgomery It is certified that error appears in the above-identified patent and that said Letters Patent is hereby corrected as shown below:

Column 6,
Line 18 "renin-angioten" should read --renin-angiotensin--.
Line 20, "renin-angioten" should read --renin-angiotensin--.

Signed and Sealed this

Fifteenth Day of August, 2006

JON W. DUDAS
*Director of the United States Patent and Trademark Office*